United States Patent
Carter et al.

(10) Patent No.: US 8,025,691 B2
(45) Date of Patent: Sep. 27, 2011

(54) SINGLE PEEL STENT INTRODUCER APPARATUS

(75) Inventors: Mathew P. Carter, Dobson, NC (US); Victor D. Clark, Winston-Salem, NC (US); John A. Karpiel, Winston-Salem, NC (US); Gregory J. Skerven, Kernersville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1197 days.

(21) Appl. No.: 11/454,607

(22) Filed: Jun. 16, 2006

(65) Prior Publication Data
US 2007/0010867 A1    Jan. 11, 2007

Related U.S. Application Data

(60) Provisional application No. 60/692,329, filed on Jun. 20, 2005.

(51) Int. Cl.
*A61F 2/06*   (2006.01)
(52) U.S. Cl. ..................................... 623/1.11
(58) Field of Classification Search ......... 623/1.11–1.13
See application file for complete search history.

(56) References Cited

U.S. PATENT DOCUMENTS

| | | | |
|---|---|---|---|
| 5,707,376 A * | 1/1998 | Kavteladze et al. | 623/1.11 |
| 7,314,481 B2 * | 1/2008 | Karpiel | 623/1.12 |
| 2005/0033402 A1 | 2/2005 | Cully et al. | 623/1.11 |
| 2005/0080476 A1 | 4/2005 | Gunderson et al. | 623/1.11 |
| 2005/0149159 A1 * | 7/2005 | Andreas et al. | 623/1.11 |

FOREIGN PATENT DOCUMENTS

| | | |
|---|---|---|
| WO | WO 98/20812 A1 | 5/1998 |
| WO | WO 2004/066809 A2 | 8/2004 |
| WO | WO 2004/080504 A2 | 9/2004 |
| WO | WO 2005/032420 A2 | 4/2005 |

* cited by examiner

*Primary Examiner* — Gary Jackson
*Assistant Examiner* — Eric Blatt
(74) *Attorney, Agent, or Firm* — Brinks Hofer Gilson & Lione (57) ABSTRACT

A stent introducer apparatus includes a handle having a housing and a rotatable reel. An inner stent carrier having a proximal end and a distal end is provided, with the proximal end being connected to the housing of the handle. An outer sheath movably disposed about the inner stent carrier and having a proximal end and a distal end is provided, with the proximal end being connected to the reel of the handle. Rotation of the reel relative to the housing peels the outer sheath away from the inner stent carrier so as to move the outer sheath proximally relative to the inner stent carrier, thereby exposing the distal end of the inner stent carrier. The inner stent carrier has a stent carrying portion at its distal end to carry a stent that is deployed when the distal end of the inner stent carrier is exposed.

17 Claims, 5 Drawing Sheets

SINGLE PEEL STENT INTRODUCER APPARATUS

RELATED APPLICATION

This application claims the benefit of priority from U.S. provisional application No. 60/692,329, filed Jun. 20, 2005, which is incorporated herein by reference.

TECHNICAL FIELD

The present invention relates to an apparatus for delivering an implantable prosthesis and, in particular, to an apparatus for introducing a stent to a desired location.

BACKGROUND OF THE INVENTION

Stents are used for a variety of applications. For example, stents are used within the biliary tree. Current biliary and pancreatic stent delivery systems generally include an introducer catheter with the stent loaded at the distal end thereof. A pusher catheter is used to deploy the stent from the distal end of the introducer catheter.

While current stent delivery systems are effective, there is a continuing need for a more effective and efficient stent delivery system. The present invention meets that need by providing an apparatus that ensures that the stent does not jump forward during deployment, and also provides enhanced accuracy of the stent deployment location.

SUMMARY OF THE INVENTION

Accordingly, the single peel stent introducer apparatus has an introducer catheter with a proximal end and a distal end, the distal end providing a self-expanding stent. More specifically, the introducer catheter includes an elongate inner stent carrier and an elongate outer sheath. The outer sheath is slidably disposed about the inner stent carrier in a coaxial arrangement. The self-expanding stent is circumferentially mounted on a distal end portion of the inner stent carrier. The self-expanding stent is maintained in a compressed pre-deployment configuration by the outer sheath. The self-expanding stent is deployed by moving the outer sheath proximally relative to the inner stent carrier a distance sufficient to expose the stent.

The single peel stent introducer apparatus further includes a handle connected to the proximal end of the introducer catheter. The handle includes housing and a reel rotatably mounted thereon. The housing includes a proximal opening and a distal opening. The coaxially arranged outer sheath and the inner stent carrier of the introducer catheter pass though the proximal opening and into an interior area of the housing. At a location within the housing, the outer sheath is separated from the inner stent carrier by splitting the wall of the outer sheath so as to allow the proximal end of the outer sheath to be peeled away from the inner stent carrier. The portion of the proximal end of the outer sheath that is separated from the inner stent carrier is connected to the reel.

The reel is configured to pull or peel the outer sheath off of and away from the inner stent carrier. More specifically, the reel includes a rotatable shaft about which the proximal end of the outer sheath is wrapped. The outer sheath is pulled or peeled away from the inner stent carrier by rotating the shaft so as to cause further separation of the outer sheath from the inner stent carrier. The shaft is spaced away from the longitudinal axis of the introducer catheter and provides a transverse peel force that is sufficient to split the wall of the outer sheath as it is being pulled away from the inner stent carrier. The shaft may include a ratchet or one-way clutch for smooth, incremental, and/or one-way rotation of the handle. A knob is preferably attached to the shaft and provides a user a mechanism for rotating the shaft.

The portion of the proximal end of the inner stent carrier that is separated from the outer sheath passes out through the distal opening of the housing. The distal opening preferably includes a clamp to prevent movement of the inner stent carrier relative to the housing. More specifically, the clamp prevents proximal movement of the inner stent carrier relative to the housing as the outer sheath is being peeled away from the inner stent carrier.

In operation, as the reel is rotated relative to the housing, the outer sheath is peeled away from the inner stent carrier. This results in proximal movement of the outer sheath relative to the housing. Because the inner stent carrier is restrained against proximal movement relative to the housing, the outer sheath is moved proximally relative to the inner stent carrier, thereby resulting in the exposure and deployment of the self-expanding stent.

The inner stent carrier may comprise a lumen extending therethrough, which may be configured for the passage of fluids or a wire guide. A wire guide is an elongate member that can be used to provide initial access to the worksite within the patient. Once the wire guide has gained access to the worksite, the proximal end of the wire guide can be inserted into the distal end of the introducer catheter by passing the wire guide into the lumen of the inner stent carrier. The introducer catheter can then be fed over the wire guide and directed to the worksite. The introducer catheter may comprise intermediate openings through the walls of the inner stent carrier and the outer sheath through which the wire guide may pass, thereby eliminating the need for the wire guide to pass through the entire length of the introducer catheter.

The single peel stent introducer apparatus may also include an irrigation adapter. The irrigation adapter includes a housing and a fluid injection port. The irrigation adapter may be a separate component or may be attached to the handle housing. The irrigation housing is configured for attachment to the proximal end of the inner stent carrier, and includes a seal for sealing about the inner stent carrier. The fluid injection port is configured for the introduction of fluid into the irrigation housing, and preferably includes a luer fitting for connection to a standard syringe. Fluid introduced through the fluid injection port passes into the lumen of the inner stent carrier. For example, a fluid such as saline may be introduced to flush air from the inner stent carrier or the self-expanding stent prior to insertion of the introducer catheter into the patient. A fluid such as contrast media may also be introduced to assist in the visualization of the worksite within the patient. The irrigation adapter may also include an exit port to allow a wire guide to pass there through and into the inner stent carrier. The exit port preferably includes a seal to seal about the wire guide.

DESCRIPTION OF THE INVENTION

Figure 1:
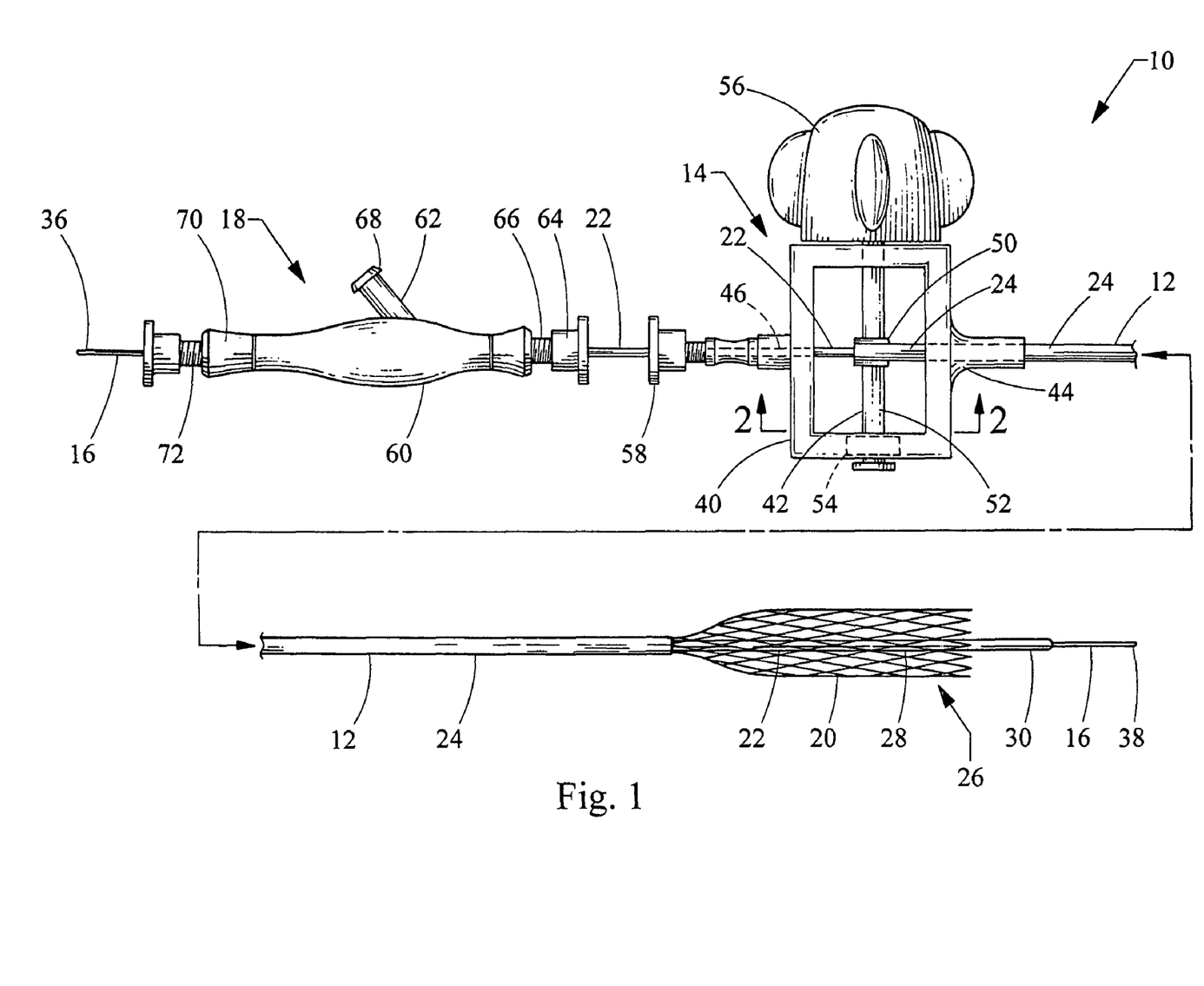
FIG. 1 is a side view of one embodiment of the present invention.
Figure 2:
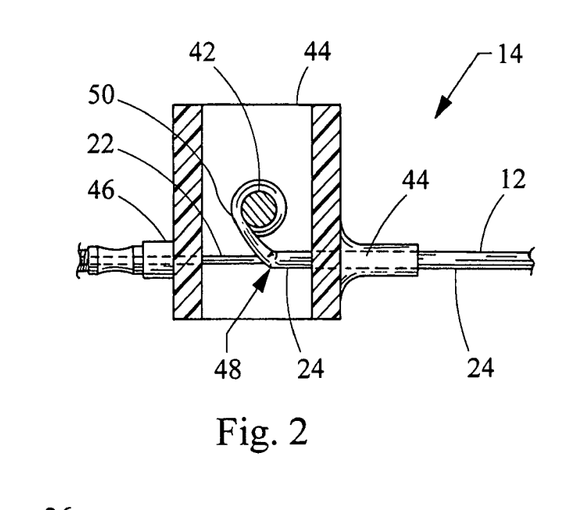
FIG. 2 is a cross-sectional view of the handle portion of the embodiment of FIG. 1 taken along line 2-2.
Figure 3:
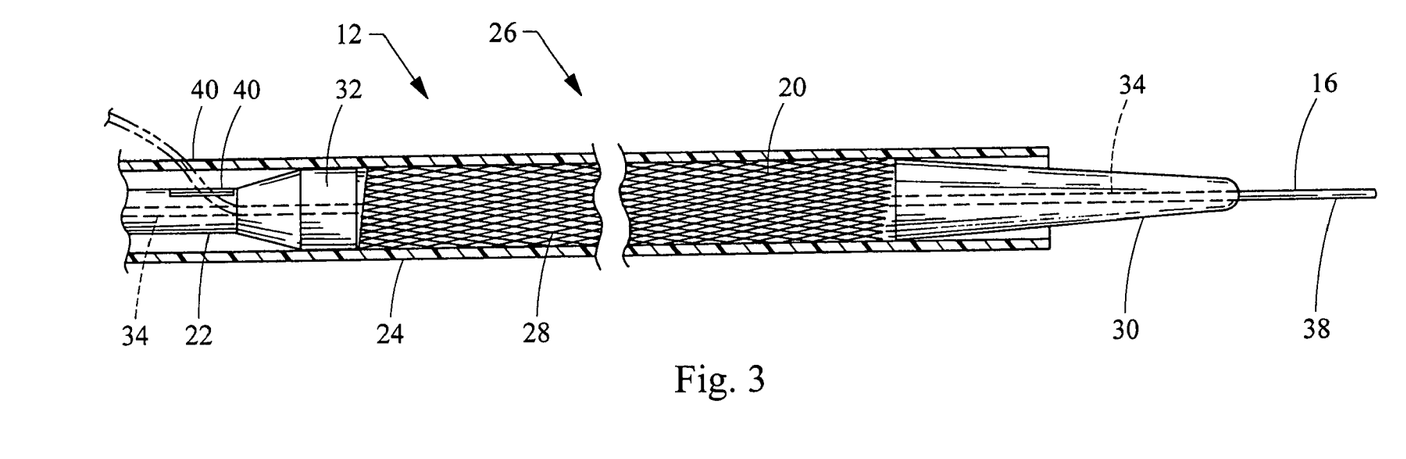
FIG. 3 is a partially sectioned view of the stent carrying portion of the introducer catheter of the embodiment of FIG. 1.

Turning now to FIGS. 1-3, one embodiment of the single peel stent introducer apparatus 10 according to the present invention is shown. The single peel stent introducer apparatus 10 includes an introducer catheter 12, a handle 14, and an irrigation adapter 18. As shown in these figures, the introducer apparatus 10 further includes a self-expanding stent 20 preloaded in the distal end of the introducer catheter 12. As will be explained in greater detail below, the handle 14 has a rotatable portion that, when rotated, causes the self-expanding stent 20 to be deployed from the introducer catheter 12. While the type of stent is not critical to the invention, preferred stents are the self-expanding biliary stent sold as SPIRAL Z™ and ZA-STENT™ sold by Wilson-Cook Medical, Inc. A wire guide 16 is also shown extending through the introducer apparatus 10. The stent 20 and the wire guide 16 are separate components from the introducer apparatus 10.

The introducer catheter 12 includes an elongate inner stent carrier 22 and an elongate outer sheath 24. The outer sheath 24 is slidably disposed about the inner stent carrier 22 in a coaxial arrangement. As best seen in FIG. 3, the stent 20 is circumferentially mounted on a distal end portion 26 of the inner stent carrier 22. The distal end portion 26 includes a stent carrying portion 28 having a reduced diameter configured to receive the self-expanding stent 20. More specifically, the stent carrying portion 28 has an outside diameter smaller than the outside diameter of the adjacent or other portions of the inner stent carrier 22 so that when the stent 20 is loaded onto the stent carrying portion 28, the resulting thickness or diameter of the stent 20 and stent carrying portion 28 is not greater than the diameter of the adjacent portions of the inner stent carrier 22. The length of the stent carrying portion 28 approximates the length of the stent 20.

The distal end portion 26 of the inner stent carrier 22 also includes an end cap 30 disposed distally of the stent carrying portion 28. The end cap 30 is preferably tapered and/or rounded towards the distal end to facilitate atraumatic passage through the lumen of the patient (not shown) as the introducer catheter 12 is directed to the patient worksite. The end cap 30 may be formed of a soft material such as a soft polymer with good bonding properties so that it can be bonded or attached to the distal end of the stent carrying portion 28 of the inner stent carrier 22. The end cap 30 may include barium sulfate or some other agent or marker to provide radiopacity to the end cap 30. The radiopacity of the end cap 30 permits the use of radiofluoroscopy equipment and techniques to assist in positioning the stent 20 within the patient worksite.

The distal end portion 26 of the inner stent carrier 22 further includes a stent pusher 32 disposed proximally of the stent carrying portion 28. The stent pusher 32 is configured to engage the proximal end of the stent 20, and prevents the stent 20 from migrating in a proximal direction relative to the inner stent carrier 22 during deployment. More specifically, the stent pusher 32 has a broad distal face that contacts the proximal end of the stent 20 to prevent the stent 20 from being pulled proximally as the outer sheath 24 is retracted relative to the inner stent carrier. The stent pusher 32 may be formed of a separate material or may be integral with the adjacent tubular portions of the inner stent carrier 22. Where it is formed of a separate material, it may be made of metal or plastic and may be secured to the tubular portions by gluing or other well known securing methods. The stent pusher 32 may also include a radiopaque marker or band. Alternatively, the stent pusher 32 may include barium sulfate or some other material to provide radiopacity. The radiopacity of the stent pusher 32 permits the use of radiofluoroscopy equipment and techniques to assist in positioning the stent 20 within the patient worksite.

The inner stent carrier 22 may be made of any suitable material such as PEEK, polyvinyl chloride (PVC), polyimide, polyimide reinforced with a stainless steel braid, polyurethane, nylon, metal tubing such as nitinol or stainless steel, and the like. The inner stent carrier 22 may also be formed as a coil or a solid-core wire guide. In one embodiment, the proximal portion of the inner stent carrier 22 is formed from nylon tubing while the distal portion, and especially the stent carrying portion 28, is formed from polyimide so as to provide the proximal and distal portions with different physical properties such as a varying stiffness or flexibility.

It the embodiment illustrated in FIGS. 1-3, the inner stent carrier 22 includes a lumen 34 extending therethrough, which may be configured for the passage of fluids or a wire guide 16. The wire guide 16 is an elongate member that can be used to provide initial access to the worksite within the patient. Once the distal end 38 of the wire guide 16 has gained access to the worksite, the proximal end 36 of the wire guide 16 can be inserted into the distal end of the introducer catheter 12 by passing the wire guide 16 into the lumen 34 of the inner stent carrier. The introducer catheter 12 can then be fed over the wire guide 12 and directed to the worksite. The introducer catheter 12 may also comprise intermediate openings or ports 40 through the walls of the inner stent carrier 22 and the outer sheath 24 through which the wire guide 16 may pass (see FIG. 3), thereby eliminating the need for the wire guide 16 to pass through the entire length of the introducer catheter 12. However, it should be understood by those skilled in the art that the inner stent carrier 22 could comprise a solid wire or catheter, often referred to as a pusher member, without a lumen 34 extending longitudinally through the interior thereof.

As best seen in FIG. 3, the stent 20 is maintained in a compressed pre-deployment configuration by the outer sheath 24. In particular, the stent 20 is disposed in a cavity formed between the outer sheath 24 and the stent carrying portion 28 of the inner stent carrier 22. The distal and proximal ends of this cavity are defined by the end cap 30 and the stent pusher 32, respectively. The stent 20 is deployed by moving or retracting the outer sheath 24 in a proximal direction relative to the inner stent carrier 22 a distance sufficient to expose the stent 20. More specifically, as the outer sheath 24 is retracted to expose the stent 20, the stent 20 is allowed to self-expand so as to engage the wall of the patient's lumen. FIG. 1 illustrates the stent 20 in a partially deployed position, wherein the outer sheath 24 has been moved proximally relative to the inner stent carrier 22.

The outer sheath 24 may be made from any suitable material and is preferably made from a clear material such as a substantially clear polymer. Although not required, transparency of the outer sheath 24 allows the user to verify that the stent 20 is properly loaded in the introducer catheter 12 prior to its insertion into the patient. Suitable materials include, but are not limited to, polytetrafluoroethylene (PTFE) and polyeretherketone (PEEK). The exterior surface of the outer sheath 24 may comprise a lubricous coating to reduce friction during the introduction and passage of the introducer catheter 12 into the patient. Likewise, the interior surface of the outer sheath 24 may comprise a lubricous coating to reduce friction with the inner stent carrier 22 as the outer sheath 24 is retracted during stent 20 deployment.

The introducer apparatus 10 further includes a handle 14 connected to the proximal end of the introducer catheter 12. The handle 14 includes housing 40 and a reel 42 rotatably mounted thereon. The housing 40 includes a proximal opening 44 and a distal opening 46. The coaxially arranged outer sheath 24 and the inner stent carrier 22 of the introducer catheter 12 pass though the proximal opening 44 and into an interior area of the housing 40. As best seen in FIG. 2, the outer sheath 24 is separated from the inner stent carrier 22 at a location within the housing 40. This is accomplished by forming a split 48 in the wall of the outer sheath 24 so as to allow the proximal end 50 of the outer sheath 24 to be peeled away from the inner stent carrier 22. A portion of the proximal end 50 of the outer sheath 24 that has been separated from the inner stent carrier 22 is then connected to and/or wrapped around the reel 42.

The reel 42 is configured to pull or peel the outer sheath 24 off of and away from the inner stent carrier 42. More specifically, the reel 42 includes a rotatable shaft 52 about which the proximal end 50 of the outer sheath 24 is wrapped. The outer sheath 24 is pulled or peeled away from the inner stent carrier 22 by rotating the shaft 52 so as to cause further splitting and separation of the outer sheath 24 away from the inner stent carrier 22. As best seen in FIG. 2, the shaft 52 is spaced away from the longitudinal axis of the introducer catheter 12 (i.e., the inner stent carrier 22) and provides a transverse peel force that is sufficient to split the wall of the outer sheath 24 as it is being pulled away from the inner stent carrier 22. The shaft 52 is configured to hold a sufficient length of the outer sheath 24 to permit complete deployment of the stent 20, as well as adjust the position of the handle 14 relative to the introducer catheter 12.

The outer sheath 24 of the embodiment illustrated is uniform and does not include any weakened areas for facilitating the splitting of the outer sheath 24 as it is pulled away from the inner stent carrier 22. This is because the handle 14 arrangement, i.e., the position of the reel 24 within the housing 40, provides a transverse peel force that is sufficient to split the wall of the outer sheath 24 as it is being pulled away from the inner stent carrier 22. Thus, the handle 14 is adaptable for use with standard introduction catheters 12 of ordinary design. However, the outer sheath 24 may alternatively comprise a thin-walled tube of a longitudinally molecularly oriented, anisotropic material such as PTFE whose molecular properties permit it to be torn longitudinally along a predetermined split line. A method for molecularly orienting is disclosed in U.S. Pat. No. 4,306,562, the relevant contents of which are incorporated herein by reference. In addition, longitudinal tearing can also be facilitated by pre-weakening the outer sheath 24 with the formation of a groove, slit or perforation in the wall of the outer sheath 24 so that the sheath tears along the groove.

The portion of the inner stent carrier 22 that is separated from the outer sheath 24, i.e., the portion that is proximal of split 48, passes out through the distal opening 46 of the housing 40. The distal opening 46 preferably includes a clamp 58 to prevent movement of the inner stent carrier 22 relative to the housing 40. More specifically, the clamp 58 prevents proximal movement of the inner stent carrier 22 relative to the housing 40 as the outer sheath 24 is being peeled away from the inner stent carrier 22. The clamp 58 is preferably releasable so as to selectively allow movement of the inner stent carrier 22, which may be advantageous for moving the handle 14 relative to the introducer catheter 12 without deploying the stent 20. In other words, releasing the clamp 58 permits the inner stent carrier 22 to be retracted simultaneously with the outer sheath 24 as the reel 42 is rotated to peel the outer sheath 24 away from the inner stent carrier 22, which has the effect of shortening the overall length of the introducer catheter 12.

With reference to FIG. 1, a knob 56 is preferably attached to the shaft 52 and provides the user a tactile and ergonomic mechanism for rotating the shaft 52. Because the diameter of the knob 56 is larger than the diameter of the shaft 52, the knob 46 also provides the user with a mechanical advantage for rotating the shaft 52. The shaft 52 may also include a ratchet or one-way clutch 54 for smooth, incremental, and/or one-way rotation of the handle. As will be explained below, these features provide improved control over the retraction of the outer sheath 24 during deployment of the stent 20.

The introducer apparatus 10 may also include an irrigation adapter 18. The irrigation adapter 18 includes a housing 60 and a fluid injection port 62. The irrigation adapter 18 may be a separate component, as shown in FIG. 1, or may be attached directly to the handle housing 40. The irrigation housing 18 is configured for attachment to the proximal end of the inner stent carrier 22, and includes a seal 66 for sealing about the inner stent carrier 22. The seal 66 preferably also includes a clamp 64 for securing the irrigation adapter 18 to the inner stent carrier 22. The fluid injection port 62 is configured for the introduction of fluid into the irrigation housing 18, and preferably includes a luer fitting 68 for connection to a standard syringe. Fluid introduced through the fluid injection port 62 passes into the lumen 34 of the inner stent carrier 22. For example, a fluid such as saline may be introduced to flush air from the inner stent carrier 22 and/or the stent 20 prior to insertion of the introducer catheter 12 into the patient. A fluid such as contrast media may also be introduced to assist in the visualization of the worksite within the patient. The irrigation adapter 18 may also include an exit port 70 to allow a wire guide 16 extending through the inner stent carrier 22 to exit the proximal end of the irrigation adapter 18. The exit port 70 preferably includes a seal 72 to seal about the wire guide 16.

Operation of the introducer apparatus 10 will now be described. The distal end of the introducer catheter 12 is delivered to the desired location, i.e., the worksite within the patient. Once the distal end of the introducer catheter 12 is in the correct position for deployment of the stent 20, the handle 14 can be advanced, if desired, distally along the introducer catheter 12. For example, it may be desirable to position the handle 14 closer to the point of entry for the introducer catheter 12 into the patient. Advancement of the handle 14 relative to the introducer catheter 12 is accomplished by releasing the clamp 58 so as to permit the inner stent carrier 22 to move proximally through the handle 14. The reel 42 is then rotated to rotated relative to the handle housing 40 so as to peel and/or pull the outer sheath 24 away from the inner stent carrier 24. This results in the proximal movement of the outer sheath 24 relative to the handle housing 40. Because the inner stent carrier 22 is not restrained against proximal movement relative to the handle housing 40, the inner stent carrier 22 moves simultaneously with the outer sheath 24. Deployment of the stent 20 does not result from this simultaneous movement of the inner stent carrier 22 and the outer sheath 24.

Once the handle 14 and the distal end of the introducer catheter 12 are in the correct position for deployment of the stent 20, the clamp 58 is closed to prevent further movement of the inner stent carrier 22 relative to the handle 14. The reel 42 of the handle 14 is then rotated relative to the handle housing 40 so as to further peel and/or pull the outer sheath 24 away from the inner stent carrier 24. This results in the proximal movement of the outer sheath 24 relative to the handle housing 40. Because the inner stent carrier 22 is restrained against proximal movement relative to the handle housing 40, the outer sheath 24 is moved proximally or retracted relative to the inner stent carrier 22. As a result, and as illustrated in FIG. 1, the stent 20 is exposed as the distal end of the outer sheath 24 is retracted proximally of the stent carrying portion 28 of the inner stent carrier 22. The reel 42 is rotated until the stent 20 is fully exposed, thereby completing the deployment of the stent 20. Thereafter, the introducer catheter 12 can be retracted from the desired location, leaving the deployed stent 20 behind.

Figure 4:
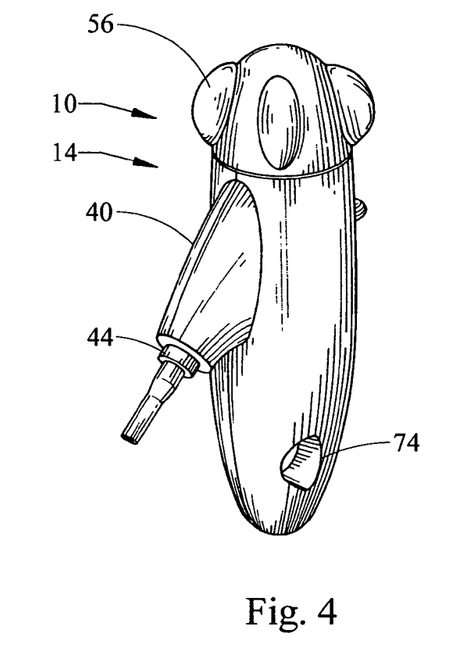
FIG. 4 is a perspective right-hand view of a second embodiment of the present invention.
Figure 5:
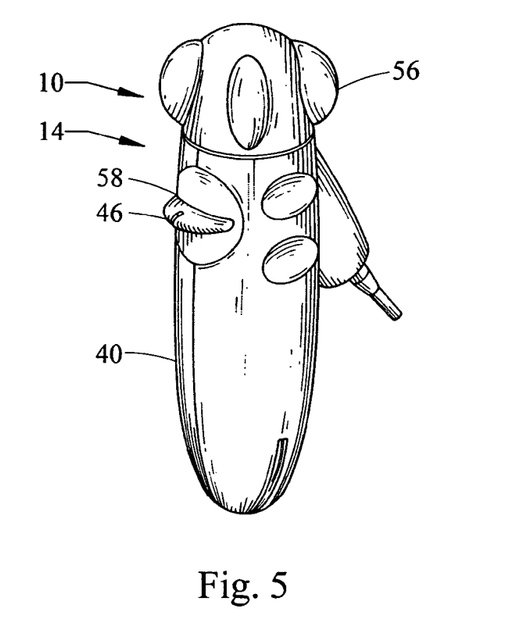
FIG. 5 is a perspective left-hand view of the embodiment shown in FIG. 4.
Figure 6:
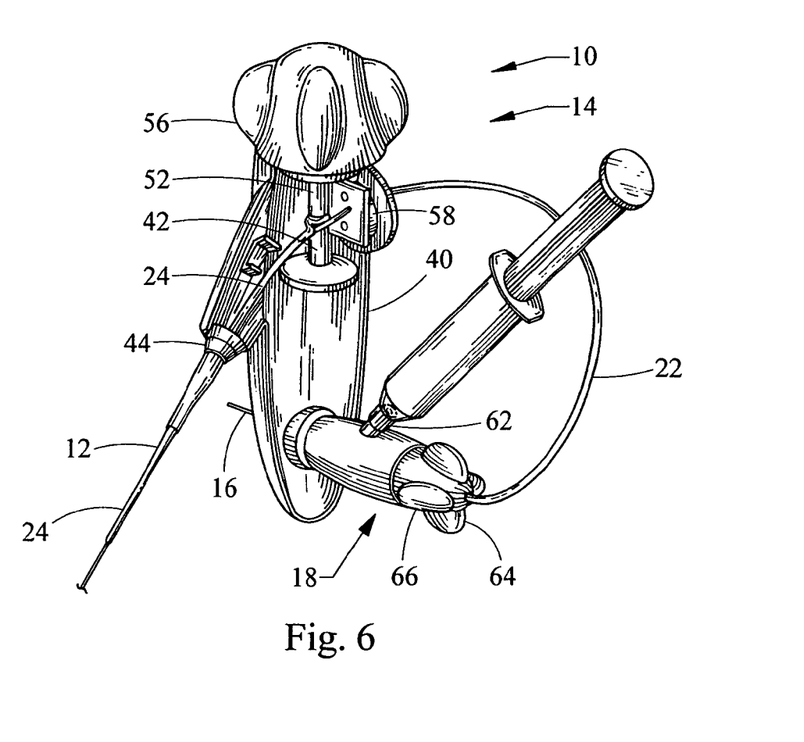
FIG. 6 is a partially sectioned perspective right-hand view of the embodiment shown in FIG. 4 and further including an irrigation adapter according to an embodiment of the present invention.

FIGS. 4-6 illustrate a second embodiment of the handle 14 according to the present invention. As best seen in the cut-away portion of FIG. 6, the handle 14 of this embodiment has the same basic functional components as the handle of the first embodiment shown in FIGS. 1-3. For example, the handle 14 comprises a reel 42 including a rotatable shaft 52 to which the outer sheath 24 is secured and wrapped. The reel 42 further includes a knob 56 for rotating the shaft 52. However, the handle 14 shown in FIGS. 4-6 has a different overall shape and physical arrangement of the components that may be more ergonomically satisfactory to some users. More specifically, the handle 14 of this embodiment includes an elongate housing 40 having a rounded shape that is easily grasped by the hand of a user. In addition, and as shown in FIGS. 4 and 6, the handle 14 includes a socket 74 configured to receive the irrigation adapter 18. Other aspects of the handle 14, including its manner of operation for deploying a stent 20 from the distal end portion of the introducer catheter 12, are similar to that of the embodiment described above in connection with FIGS. 1-3.

Figure 7:
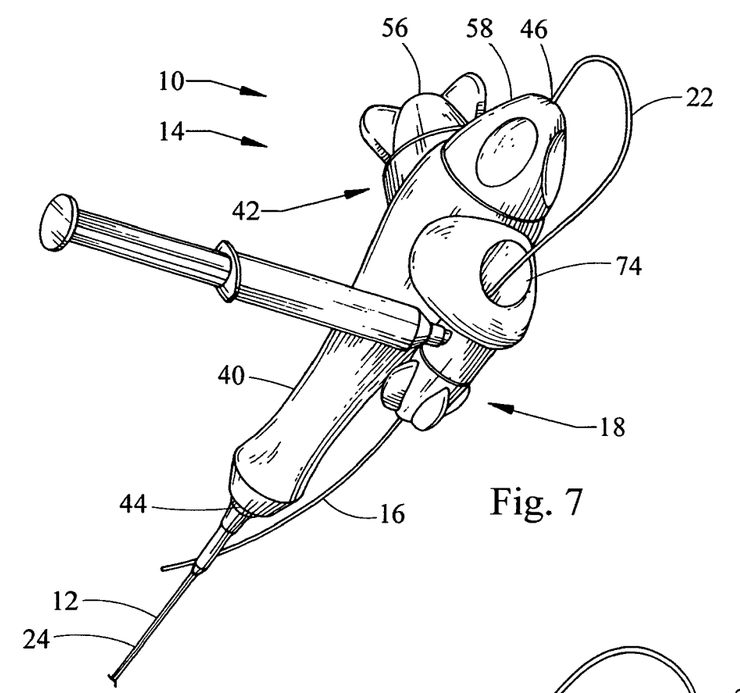
FIG. 7 is a perspective right-hand view of a third embodiment of the present invention.
Figure 8:
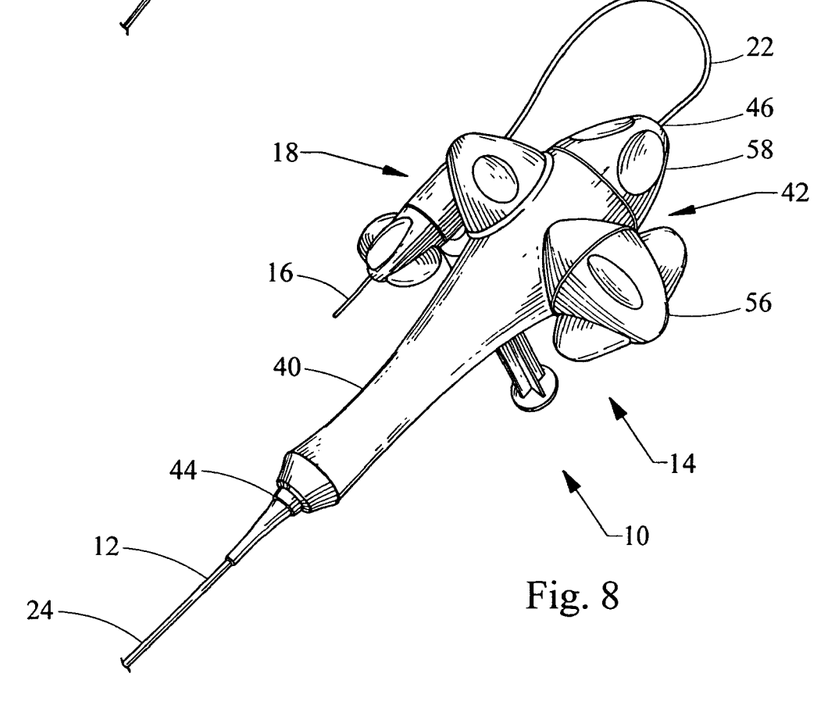
FIG. 8 is a perspective left-hand view of the embodiment shown in FIG. 7.

FIGS. 7-8 illustrate a third embodiment of the handle 14 according to the present invention. The handle 14 of this embodiment has the same basic functional components as the handle of the first embodiment shown in FIGS. 1-3. For example, the handle 14 comprises a reel 42 including a rotatable shaft (not shown) to which the outer sheath 24 is secured and wrapped. The reel 42 further includes a knob 56 for rotating the shaft. However, the handle 14 shown in FIGS. 7-8 has a different overall shape and physical arrangement of the components that may be more ergonomically satisfactory to some users. More specifically, the handle 14 of this embodiment includes an elongate housing 40 having a concaved shape that is easily grasped by the hand of a user. In addition, the handle 14 includes a socket 74 configured to receive the irrigation adapter 18. Other aspects of the handle 14, including its manner of operation for deploying a stent 20 from the distal end portion of the introducer catheter 12, are similar to that of the embodiment described above in connection with FIGS. 1-3.

Figures 9, 10:
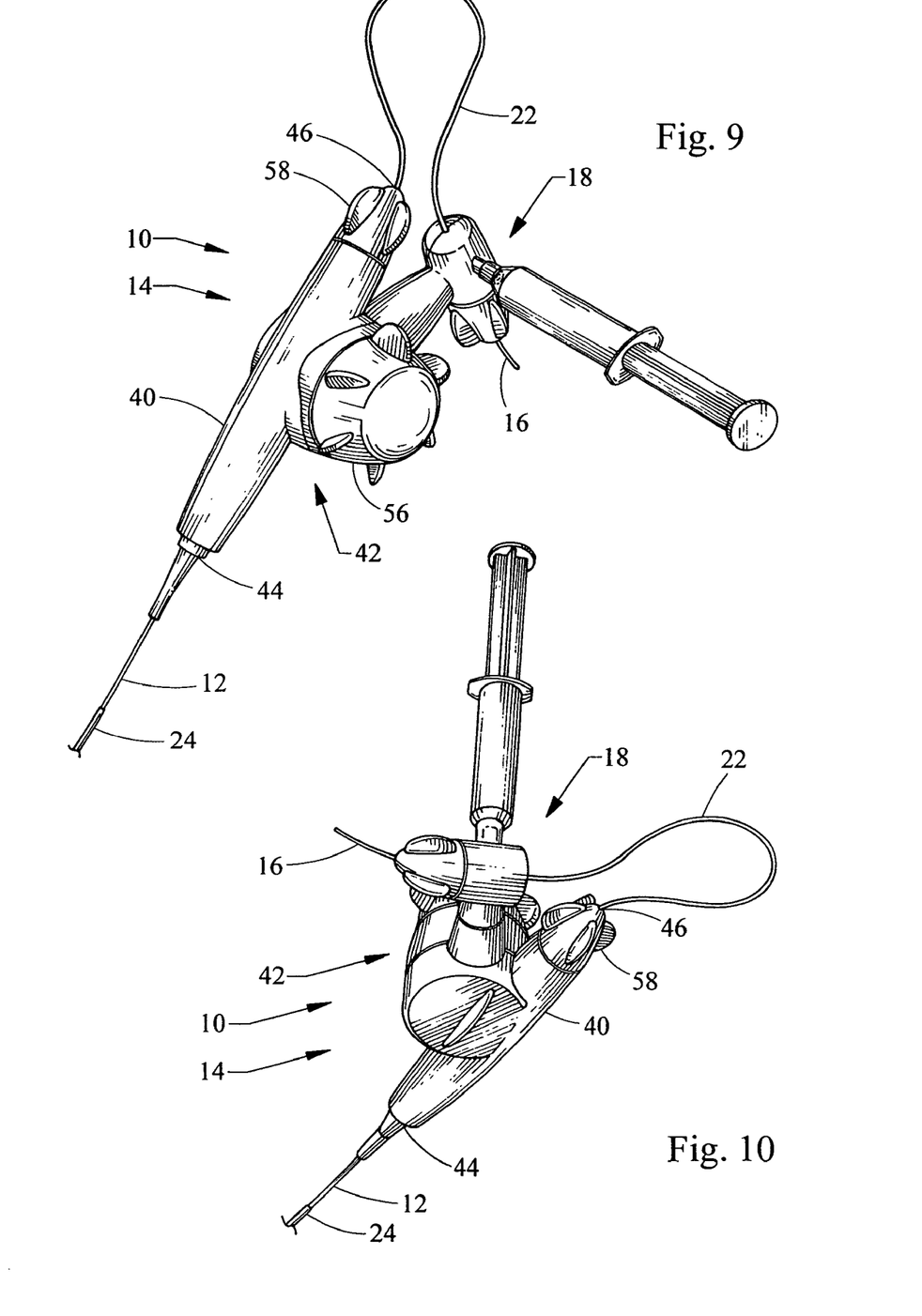
FIG. 9 is a perspective right-hand view of a fourth embodiment of the present invention.
FIG. 10 is a perspective left-hand view of the embodiment shown in FIG. 9.

FIGS. 9-10 illustrate a fourth embodiment of the handle 14 according to the present invention. The handle 14 of this embodiment has the same basic functional components as the handle of the first embodiment shown in FIGS. 1-3. For example, the handle 14 comprises a reel 42 including a rotatable shaft (not shown) to which the outer sheath 24 is secured and wrapped. The reel 42 further includes a knob 56 for rotating the shaft. However, the handle 14 shown in FIGS. 7-8 has a different overall shape and physical arrangement of the components that may be more ergonomically satisfactory to some users. More specifically, the handle 14 of this embodiment includes an elongate housing 40 having a cylindrical shape that is easily grasped by the hand of a user. In addition, irrigation adapter 18 is permanently affixed to the handle 14. Other aspects of the handle 14, including its manner of operation for deploying a stent 20 from the distal end portion of the introducer catheter 12, are similar to that of the embodiment described above in connection with FIGS. 1-3.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A stent introducer apparatus comprising:
an elongate outer sheath having a proximal end portion and a distal end portion;
an elongate inner stent carrier movably disposed within the outer sheath, the inner stent carrier having a proximal end portion and a distal end portion;
a deployable stent, the stent being disposed within the distal end portion of the outer sheath and being engaged by the distal end portion of the inner stent carrier; and
a handle comprising a housing and a rotatable reel, the proximal end portion of the outer sheath being connected directly to the reel, and the proximal end portion of the inner stent carrier being connected to the housing,
wherein the inner stent carrier is fixed against longitudinal movement relative to the handle, and the outer sheath is longitudinally movable relative to the handle,
wherein the proximal end portion of the outer sheath is splittable along a single side thereof to facilitate lateral separation from the proximal end portion of the inner stent carrier in response to a transversely applied pulling force; and
wherein the stent is deployed by rotating the reel relative to the housing so as to peel the proximal end portion of the outer sheath away from the proximal end portion of the inner stent carrier, the proximal end portion of the outer sheath being laterally separated from the inner stent carrier and wrapped around the reel as the reel is rotated, the distal end portion of the outer sheath being moved in a proximal direction relative to the distal end portion of the inner stent carrier as the proximal end portion of the outer sheath is peeled away from the proximal end portion of the inner stent carrier.

2. The stent introducer apparatus according to claim 1, wherein the proximal end portion of the inner stent carrier extends completely through the housing and is secured thereto by a releasable clamp.

3. The stent introducer apparatus according to claim 1, wherein the reel comprises a shaft having an axis of rotation that is transverse to a longitudinal axis of the proximal end portion of the inner stent carrier, the proximal end portion of the outer sheath being fixedly connected to the shaft and configured to be wrapped about the shaft as the reel is rotated.

4. The stent introducer apparatus according to claim 3, wherein the axis of rotation is spaced away from the longitudinal axis of the proximal end portion of the inner stent catheter.

5. The stent introducer apparatus according to claim 3, wherein the reel further comprise a knob attached to the shaft, the knob having a diameter that is larger than a diameter of the shaft.

6. The stent introducer apparatus according to claim 1, wherein the proximal end portion of the outer sheath is wrapped around the reel.

7. The stent introducer apparatus according to claim 1, wherein the reel includes a clutch for regulating the rotation of the reel relative to the housing.

8. The stent introducer apparatus according to claim 7, wherein the clutch limits rotation of the reel to a single rotational direction.

9. The stent introducer apparatus according to claim 7, wherein the clutch comprises a one-way ratchet that provides incremental rotation in a single rotational direction.

10. The stent introducer apparatus according to claim 1, wherein the distal end portion of the inner stent carrier comprises a stent carrying portion adapted to receive the stent, and further comprises a stent pusher adapted to engage a proximal end of the stent.

11. The stent introducer apparatus according to claim 10, wherein the distal end portion of the inner stent carrier further comprises an end cap, said end cap being disposed adjacent to a distal end of the stent.

12. The stent introducer apparatus according to claim 1, wherein the stent comprises a self-expanding stent having a compressed configuration and an expanded deployed configuration, the stent assuming the compressed configuration when disposed within the distal end portion of the outer sheath.

13. The stent introducer apparatus according to claim 1, wherein the inner stent carrier comprises a lumen extending longitudinally there through.

14. The stent introducer apparatus according to claim 13, further comprising a wire guide movably disposed through the lumen of the inner stent carrier.

15. The stent introducer apparatus according to claim 13, further comprising an irrigation adapter, the irrigation adapter being configured to permit the introduction of a fluid into the lumen of the inner stent carrier.

16. A method of deploying a stent within a body lumen of a patient, the method comprising the steps of:
a) providing a stent introducer apparatus comprising an outer sheath having a proximal end portion and a distal end portion, an inner stent carrier movably disposed within the catheter, the inner stent carrier having a proximal end portion and a distal end portion, a stent disposed within the distal end portion of the outer sheath and engaged by the distal end portion of the inner stent carrier, and a handle comprising a housing and a rotatable reel, the proximal end portion of the outer sheath being connected to reel, and the proximal end portion of the inner stent carrier being connected to the housing;
b) positioning the distal end portion of the outer sheath at a deployment location within the body lumen of the patient;
c) grasping the housing of the handle so as to hold the inner stent carrier in a relatively stationary position; and
d) rotating the reel of the handle so as to peel the proximal end portion of the outer sheath away from the proximal end portion of the inner stent carrier, thereby moving the distal end portion of the outer sheath in a proximal direction relative to the distal end portion of the inner stent carrier so as to deploy the stent from the distal end portion of the outer sheath, wherein a wall of the proximal end portion of the outer sheath is split as it is peeled away from the proximal end portion of the inner stent carrier by a transversely exerted force applied by the reel to the proximal end portion of the outer sheath as the reel is rotated.

17. The method according to claim 16, wherein the reel comprises a shaft having an axis of rotation that is transverse to and spaced away from a longitudinal axis of the proximal end portion of the inner stent carrier, and wherein rotation of the shaft causes the proximal end portion of the outer sheath to be split and peeled away from the proximal end portion of the inner stent carrier.

\* \* \* \* \*